(12) United States Patent
Hörnfeldt et al.

(10) Patent No.: US 7,376,465 B2
(45) Date of Patent: May 20, 2008

(54) MODULAR IMPLANTABLE MEDICAL DEVICE AND MANUFACTURING METHOD THEREFOR

(75) Inventors: Martin Hörnfeldt, Järfalla (SE); Björn Sjögren, Fjördhundra (SE); Eva Skoog Andersson, Tyresö (SE); Eva Micski, Huddlinge (SE); Olof Stegfeldt, Älta (SE)

(73) Assignee: St. Jude Medical AB, Jarfalla (SE)

( * ) Notice: Subject to any disclaimer, the term of this patent is extended or adjusted under 35 U.S.C. 154(b) by 234 days.

(21) Appl. No.: 10/515,757

(22) PCT Filed: Apr. 17, 2003

(86) PCT No.: PCT/SE03/00636

§ 371 (c)(1),
(2), (4) Date: Nov. 24, 2004

(87) PCT Pub. No.: WO03/092809

PCT Pub. Date: Nov. 13, 2003

(65) Prior Publication Data

US 2005/0228456 A1    Oct. 13, 2005

(30) Foreign Application Priority Data

Apr. 30, 2002   (SE) .................................. 0201321

(51) Int. Cl.
*A61N 1/02* (2006.01)
(52) U.S. Cl. ....................................... 607/36; 607/116
(58) Field of Classification Search .................. 607/36, 607/116
See application file for complete search history.

(56) References Cited

U.S. PATENT DOCUMENTS

| | | | |
|---|---|---|---|
| 4,785,827 A | 11/1988 | Fischer | |
| 5,103,818 A | 4/1992 | Maston et al. | |
| 5,314,451 A * | 5/1994 | Mulier | 607/33 |
| 5,370,669 A | 12/1994 | Daglow et al. | |
| 5,814,091 A | 9/1998 | Dahlberg et al. | |
| 5,919,215 A | 7/1999 | Wiklund | |
| 6,042,624 A * | 3/2000 | Breyen et al. | 29/25.03 |

* cited by examiner

*Primary Examiner*—Carl Layno
*Assistant Examiner*—Deborah Malamud
(74) *Attorney, Agent, or Firm*—Schiff Hardin LLP

(57) ABSTRACT

In an implantable medical device and a manufacturing method therefore, the implantable medical device has at least an electronics module and a battery module, each contributing functionally as well as to the shape of the outer enclosure of the implantable medical device. Different modules, and different versions of different modules, can be combined in different combinations, according to a device specification, to form different medical devices.

9 Claims, 3 Drawing Sheets

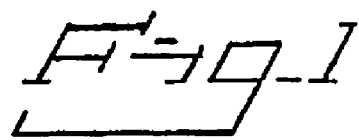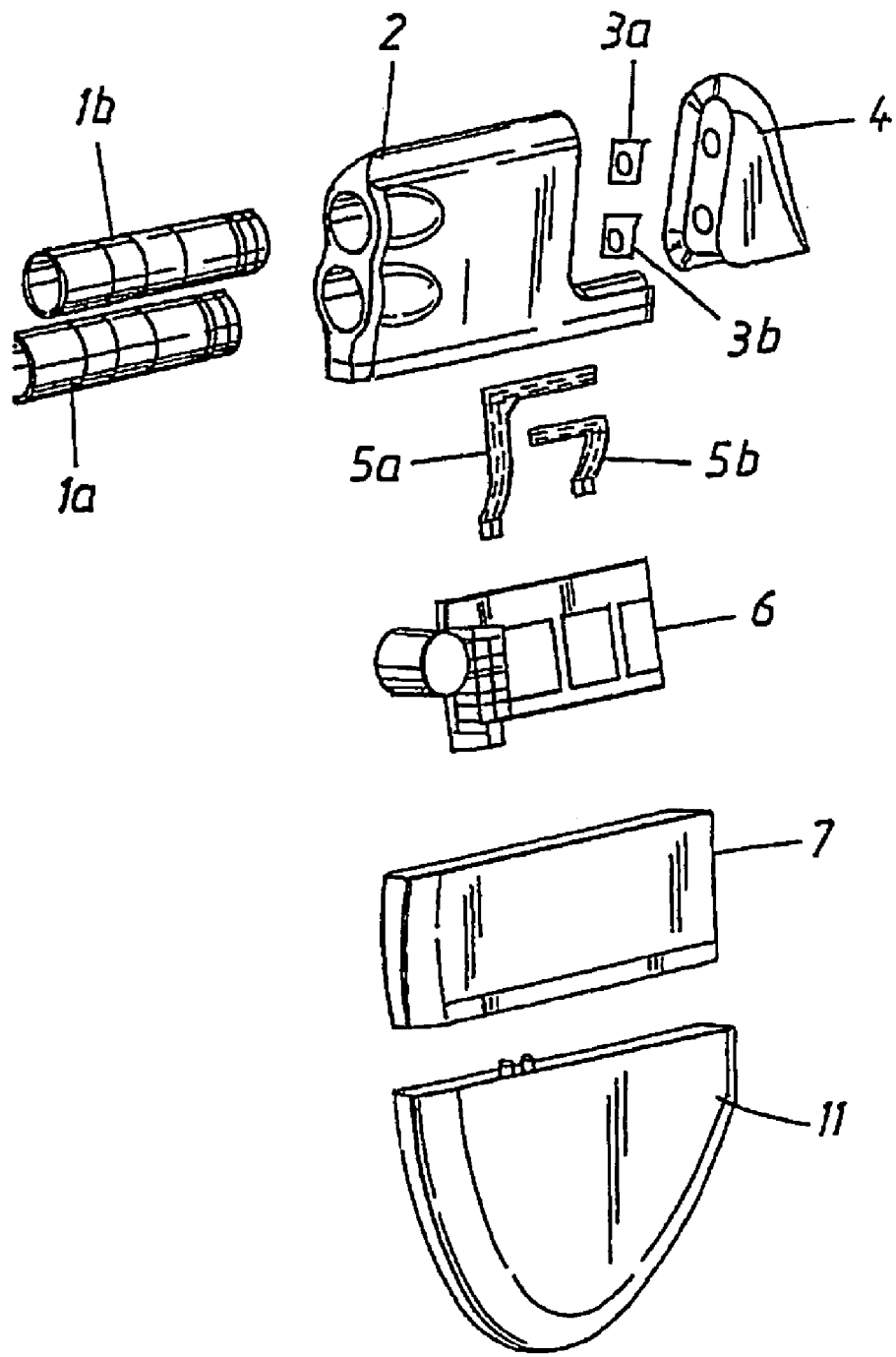

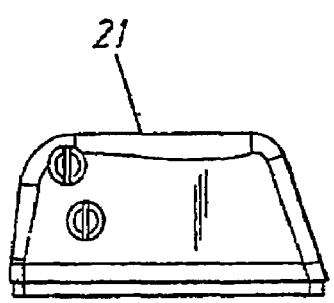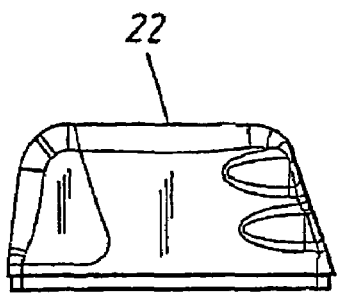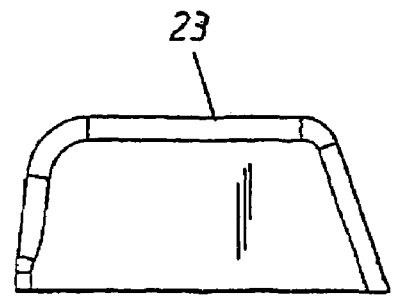
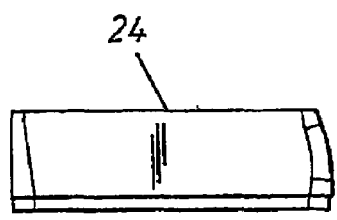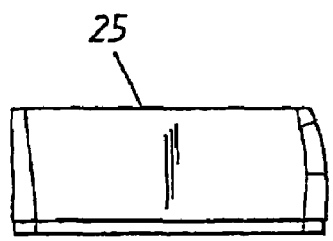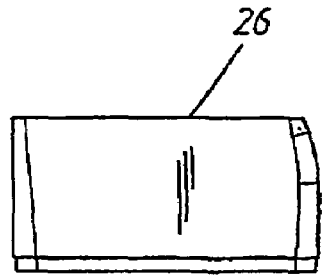
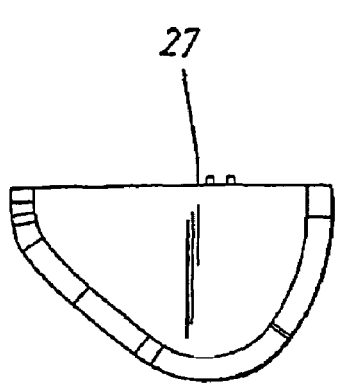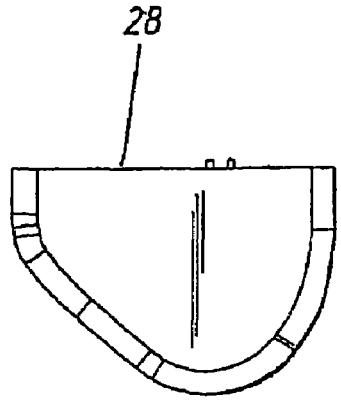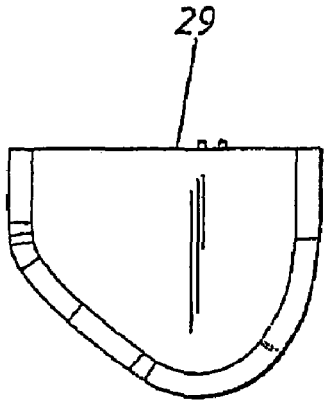

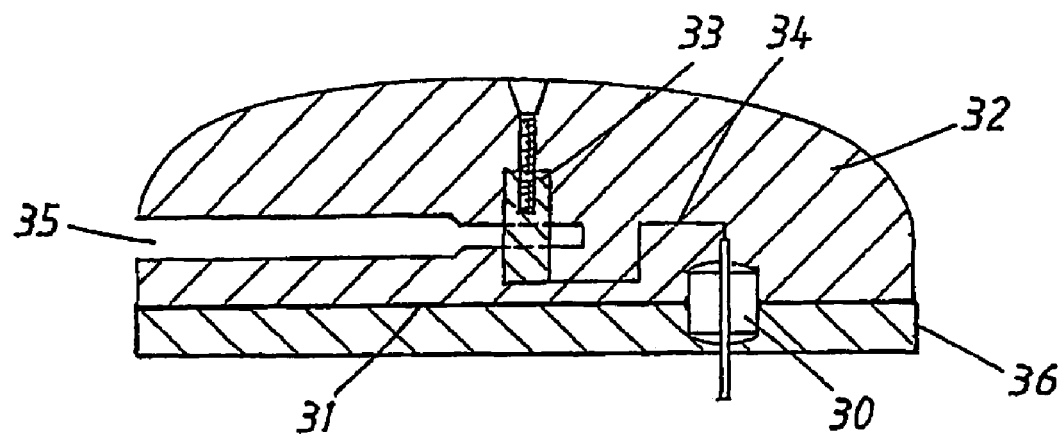
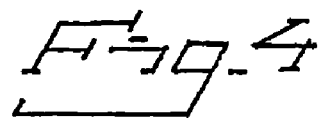
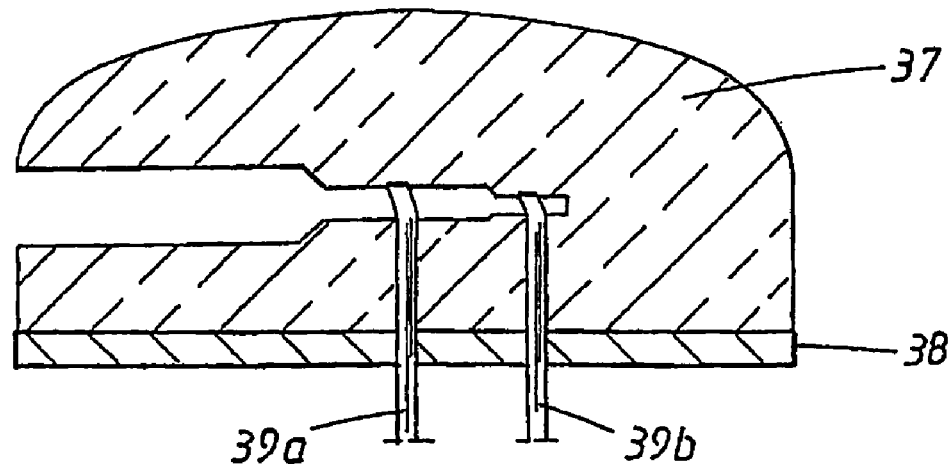

MODULAR IMPLANTABLE MEDICAL DEVICE AND MANUFACTURING METHOD THEREFOR

BACKGROUND OF THE INVENTION

1. Field of the Invention

The present invention relates to an implantable medical device and a manufacturing method therefore, of the type wherein the device is assembled from modules.

2. Description of the Prior Art

Several different ways to modularize and manufacture an implantable medical device are known.

U.S. Pat. No. 5,370,669 describes an implantable defibrillator in which the components of the active implantable device are housed within an implantable casing having three orthogonal dimensions of height, width and thickness. The height and width are substantially greater than the implantable defibrillator comprises three major subsystems, specifically, the batteries, the power capacitors, and the electronics. The three sub-systems lie respectively in parallel height-width planes, each plane being adjacent another in the thickness dimension.

U.S. Pat. No. 5,103,818 describes an arrangement that enables rapid and effective termination of electrical junctions for an implantable medical device such as a heart pacemaker or an implantable defibrillator. The electronics subsystem and the battery are placed in one half of the housing that also contains the feedthrough. At this moment the battery and the feedthrough contact the electronics subsystem via female connectors on the electronics subsystem. The electrical connections are then fused welded. Following the fusion weld of the electrical connections the other half of the housing is mounted and the enclosure welded to become hermetic.

U.S. Pat. No. 5,814,091 describes an arrangement in which the battery is integrated with the outer enclosure of the implantable medical device.

SUMMARY OF THE INVENTION

An object of the present invention is to provide a modularized device allowing economically feasible manufacture of a large number of models of an implantable medical device and while limiting the number of components needed for the entire model program.

A further object is to simplify the process of assembling the finished product.

A still further object is to shorten the development time for new products.

A still further object is to minimize the number of parts required for the completed implantable medical device.

The above objects are achieved in accordance with the invention by an implantable medical device and a manufacturing method therefor wherein the implantable device is divided into modules, each of the modules forming a portion of the outer shape of the implantable medical device, and each of the modules performing (only) a well defined function of the implantable device. A very important aspect is that one of the modules can be modified without any need to modify any of the other modules. The modules themselves have an open interface to other modules and as a consequence the modules themselves are not hermetically sealed but hermetic sealing will be obtained when the modules are permanently attached to each other by e.g. laser welding. This will make it easy to develop and manufacture different models of the implantable medical device that have different connector modules or different battery modules with a minimal cost for product development. If there are e.g. three different battery modules available, three different connector modules and three different electronics modules available then 27 different models of the finished products can be manufactured from the nine available modules. This will make it much easier for the manufacturer to adapt the production to varying market demands on battery capacity or on connector type. It is also possible to upgrade production with a more advanced electronics module while connector module and battery module remain unchanged.

The present invention is particularly suitable for use in an implantable cardioverter defibrillator (ICD). In the ICD application the requirements regarding longevity and shock energy may vary significantly depending on market requirements. One possible modularization for an ICD is to divide the ICD into four different modules according to the invention. The individual modules may be as follows: module (a) could essentially be a connector subsystem, module (b) could essentially be a power electronics subsystem including shock energy storage capacitors, power transformers etc, module (c) could essentially be low voltage electronics such as pacing/sensing circuitry, module (d) could essentially be a battery subsystem. By varying the size of module (b) with the power electronics subsystem the shock energy can be adapted to different needs through the use of shock energy capacitors of different capacitance. By varying the size of module (d) the battery subsystem capacity the can be adapted to different requirements regarding longevity and number of shocks available. It is also feasible to use a general set of modules suitable for pacemakers and for ICD's. In a bradycardia pacemaker (a), (c) and (d) would be used while in an ICD modules (a), (b), (c), and (d) would be used. The invention can also be utilized to add features to a standard pacemaker or ICD. As an example a diagnostic data collection module could be added to a standard pacemaker or ICD.

BRIEF DESCRIPTION OF THE DRAWINGS

FIG. 1 schematically illustrates an implantable medical device in accordance with the invention.

FIG. 2 shows how the manufacturing method can be implemented using three different types for each of the three different modules necessary for the production of an implantable medical device.

FIG. 3 is a sectional view of a first type of connector module for use in the implantable medical device of the invention.

FIG. 4 is a sectional view of a second type of connector module for use in the implantable medical device of the invention.

DESCRIPTION OF PREFERRED EMBODIMENTS

FIG. 1 shows an example of an implantable cardiac pacemaker built according to the invention. In this embodiment the cardiac pacemaker is manufactured using three modules. Each of the modules contributes functionally as well as to the shape of the enclosure of the implantable medical device. The following modules are used in this particular cardiac pacemaker: connector module 1a,1b,2,3a, 3b,4, electronics module 5a, 5b,6,7 and battery module 11.

The connector module 1a,1b,2,3a,3b,4 in this example is of the type in which the lead connectors are integrated into the housing without a molded plastic connector top. The connector module comprises the following parts: metallic/ceramic connector tubes 1a,1b, a portion 2 of the outer enclosure of the cardiac pacemaker, lead pin locking washers 3a,3b, a transparent plastic component 4, and flex circuits 5a,5b. The metallic/ceramic connector tubes may for example be of the type disclosed in international publication WO 00/12174. The flex circuits 5a,5b provides electrical connection between the metallic/ceramic lead connecting tubes 1a,1b and the electronics module 6. During manufacture the flex circuits 5a,5b are welded to a feedthrough portion of the connector tubes 1a,1b. The end portions of the connecting tubes 1a,1b are made of metal and are adapted to be welded in both ends to the enclosure portion 2. Each of the flex circuits 5a,5b is rolled on a connector tube and then the connector tube is inserted into the enclosure portion 2. After inserting the flex circuit 5a,5b it is rolled out and the connector tube 1a,1b is welded in both ends to the enclosure portion 2. The final step in assembling the connector module is to mount the locking washers 3a,3b and the transparent plastic component 4. The purpose of the plastic component 4 is to provide visible confirmation that the lead connecting pin is fully inserted into the implantable cardiac pacemaker at the time of implantation. The finished connector module is a complete connector for the implanted lead, as well as a part of the outer shape of the enclosure of implantable device and it is adapted for a quick electrical connection to an electronics module. During manufacture it is simply connected to the electronics module and then welded to the outer enclosure portion 7 of the electronics module. To facilitate manufacturing the enclosure portion 2 of the connector module and enclosure portion 7 of the electronics module should be designed so that they have a very good fit to each other. Preferably outer enclosure portions such as 2 and 7 mentioned above should have a mechanical click action when they are properly oriented in relation to each other.

The electronics module 6,7 comprises an electronic circuit 6 and a portion of the enclosure 7. The electronics circuit 6 should preferably be fixed to the enclosure portion 7 through gluing, or molding or other method. The electronic circuit 6 has a connection arrangement for a quick electrical connection of the connector top and the battery. This connection arrangement should preferably be of a snap in type in order to make welding, soldering or other more complicated connection methods unnecessary, but these other connection methods nevertheless can be used in the inventive device and method.

The battery module 11 serves as a power source as well as a portion of the outer enclosure. In a preferred embodiment the battery's enclosure is manufactured from titanium or any metal suitable for direct contact with tissue. In that case the electrochemical potential of the battery enclosure will become the enclosure potential of the implantable cardiac pacemaker. Thus one of the battery's electrical terminals is in direct contact with the patient's body tissue. This arrangement is particularly suitable for Lithium/Carbon Monofluoride batteries that can be manufactured with an enclosure of titanium. The outer enclosure of the battery module 11 should preferably extend slightly above the lid of the battery so that the outer encapsulation portion 7 of the electronics module 5a,5b,6,7 can be welded directly to the enclosure of the battery module 11 with no risk of jeopardizing the hermetic sealing of the battery during welding. In a more conventional embodiment an isolation layer is provided between the battery and the outer surface of the battery module to be able to more freely decide the electrical potential of the finished implantable device's enclosure.

FIG. 2 is a schematic drawing indicating how an implantable medical device can be built from different modules. The modules include a conventional connector top 21 and a connector module 22 of the type described above that has no conventional molded connector top and a closed connector top 23 without the feature of visual confirmation that the lead is properly inserted. The conventional connector top 21 has a lower metallic portion with a connector top bottom and a flange to allow it to be welded to the electronic module 24, 25, 26. The metallic portion has conventional feedthroughs to allow an electric connection between the electronic module 24, 25, 26 and the electrode lead connectors in the connector top without compromising hermetic sealing. The connector top 21 alternatively can be manufactured in a ceramic material. In the latter case there must be a metallic flange to allow welding of the connector top to the remainder of the encapsulation. Feedthroughs are not necessary if the connector top is manufactured in a ceramic material. Connection wires for connection between electrode lead connectors and the electronic module will be located inside the ceramic material in a fashion similar to a conventional feedthrough. 24, 25 and 26 represent electronic modules of different size and shape. 27, 28 and 29 represent battery modules of different size and capacity and also possible different electrochemical composition.

FIG. 3 shows the connector module 21 in a more detailed fashion. The top portion of the connector top is exactly similar to a conventional connector top. The metallic lower portion 31 has a bottom of the connector top and a flange 36 used to weld the connector top 21 to an electronics module 24, 25, 26. A feedthrough is welded to the lower metallic portion. The top portion has a conventional molded portion 32, connector block with setscrew 33, a wire connection 34 for connection between connector block 33 and feedthrough 30.

FIG. 4 shows a more detailed view of a connector module manufactured of a ceramic material. The top portion of the connector top is manufactured in a ceramic material $Al_2O_3$. Metal ribbons 39a, 39b provides electrical connection between a heart electrode connector and the electronics modules 24,25,26 with hermetic sealing of the enclosure for the electronics being maintained. A metal rim 38 is soldered to the lower portion of the connector module. The connector module is welded to the electronics module 24,25,26 by welding to the metal rim 38.

Every battery module 27,28,29 can be combined with every electronics module 24,25,26 and every electronics module can be combined with every connector module 21,22,23. Thus 27 different models of the implantable medical device can be produced using 9 different modules. This technique will make it easier to tailor the production to requirements from the market. If, for example, one market requires a particular battery size or battery capacity the battery module can easily be replaced with a suitable module while no other changes have to be made. The connector modules 21,22,23 can also be used for implantable medical devices having a conventional encapsulation.

Although modifications and changes may be suggested by those skilled in the art, it is the invention of the inventors to embody within the patent warranted heron all changes and modifications as reasonably and properly come within the scope of their contribution to the art.

We claim as our invention:

1. An implantable medical device comprising:
   at least two functional subsystems each comprising at least one component and each formed as a non-hermetically sealed module having a module encapsulation that completely covers said at least one component, at least one of said subsystems and the module thereof being available in multiple, different versions;

each module comprising an interface portion having a configuration allowing that module to mate with a corresponding interface portion of any of the multiple versions of another of said modules, said modules being mechanically connected to each other at said interface portions when mated;

the respective module encapsulations of said modules, when mechanically connected to each other, forming respective portions of an outer enclosure of a complete medical device formed by said modules; and mechanical connections that permanently mechanically connect said respective module encapsulations with one another to hermetically seal said outer enclosure.

2. A medical device as claimed in claim 1 wherein said plurality of modules comprise a module comprising a battery subsystem, a module comprising an electronic subsystem and a module comprising a connector subsystem.

3. A medical device as claimed in claim 1 wherein said plurality of modules includes a module comprising a battery subsystem, said module encapsulation of said module comprising said battery subsystem being at a potential equal to a potential of said outer enclosure of said complete medical device.

4. A medical device as claimed in claim 1 wherein said plurality of modules includes a module comprising a battery subsystem, said module encapsulation of said module comprising said battery subsystem being at a potential isolated from a potential of said outer enclosure of said complete medical device.

5. A medical device as claimed in claim 1 wherein said plurality of modules include a module comprising a battery subsystem utilizing a battery chemistry selected from the group consisting of lithium-iodine, lithium-silver vanadium oxide, lithium-carbon monofluoride, and a combination of lithium-silver vanadium oxide and lithium-carbon monofluoride.

6. A medical device as claimed in claim 1 wherein said plurality of modules includes a module comprising a battery subsystem, and wherein the module encapsulation of the module comprising said battery subsystem forms a portion of said outer enclosure of said complete medical device.

7. A medical device as claimed in claim 1 wherein said plurality of modules includes a module comprising a connector subsystem, said module comprising said connector subsystem being selected from the group consisting of a module comprising a connector subsystem with one pacing/sensing terminal, a module comprising a connector subsystem with two pacing/sensing terminals, a module comprising a connector subsystem with three pacing/sensing terminals, and a module comprising a connector subsystem with four pacing/sensing terminals.

8. A medical device as claimed in claim 1 wherein said plurality of modules includes a module comprising a electronics subsystem, said module comprising said electronics subsystem being selected from the group consisting of a module comprising a electronics subsystem with one pacing/sensing terminal, a module comprising a electronics subsystem with two pacing/sensing terminals, a module comprising a electronics subsystem with three pacing/sensing terminals, and a module comprising a electronics subsystem with four pacing/sensing terminals.

9. A medical device as claimed in claim 1 wherein said mechanical connections are laser welds.

* * * * *